(12) United States Patent
Keyes et al.

(10) Patent No.: US 12,102,773 B2
(45) Date of Patent: Oct. 1, 2024

(54) CATHETER ELEMENTS FOR BOND-STRENGTH ENHANCEMENT

(71) Applicant: Biosense Webster (Israel) Ltd., Yokneam (IL)

(72) Inventors: Joseph Thomas Keyes, Sierra Madre, CA (US); Kevin Justin Herrera, West Covina, CA (US); Christopher Thomas Beeckler, Brea, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 184 days.

(21) Appl. No.: 16/022,548

(22) Filed: Jun. 28, 2018

(65) Prior Publication Data

US 2020/0001042 A1  Jan. 2, 2020

(51) Int. Cl.
*A61M 25/00* (2006.01)
*A61B 5/00* (2006.01)
(Continued)

(52) U.S. Cl.
CPC ....... *A61M 25/0013* (2013.01); *A61B 5/6852* (2013.01); *A61B 18/1492* (2013.01);
(Continued)

(58) Field of Classification Search
CPC .......... A61M 25/0013; A61M 25/0054; A61M 25/00138; A61M 25/005; A61M 25/0052;
(Continued)

(56) References Cited

U.S. PATENT DOCUMENTS 4,398,910 A    8/1983  Blake et al.
5,372,587 A *  12/1994 Hammerslag ..... A61M 25/0144
                                                   604/95.04
(Continued)

FOREIGN PATENT DOCUMENTS

CN        1249804 A    4/2000
CN      108010807 A    5/2018
(Continued)

OTHER PUBLICATIONS

International Search Report dated Dec. 9, 2019, International Application No. PCT/IB2019/055360.
(Continued)

*Primary Examiner* — Nathan R Price
*Assistant Examiner* — Tania Ismail
(74) *Attorney, Agent, or Firm* — Troutman Pepper Hamilton Sanders LLP

(57) ABSTRACT

A catheter manufacturing method includes the step of providing a hollow cylindrical part of a catheter, having a longitudinal axis, to be bonded to a given part along respective edge surfaces of the hollow cylindrical and the given parts. One or more undercut structures that are disposed circumferentially with respect to the longitudinal axis and also generally parallel to the longitudinal axis, the undercut structures having a radial orientation with respect to the longitudinal axis, are formed at least in the edge surface of the hollow cylindrical part. The hollow cylindrical part and the given part are connected using the undercut structures.

14 Claims, 5 Drawing Sheets

(51) Int. Cl.
*A61B 18/14* (2006.01)
*A61M 25/10* (2013.01)
*A61B 18/00* (2006.01)
*A61M 25/01* (2006.01)
*A61M 39/10* (2006.01)

(52) U.S. Cl.
CPC ...... *A61M 25/0054* (2013.01); *A61M 25/104* (2013.01); *A61B 2018/00172* (2013.01); *A61B 2018/00178* (2013.01); *A61B 2018/00357* (2013.01); *A61B 2018/00577* (2013.01); *A61M 25/005* (2013.01); *A61M 25/0052* (2013.01); *A61M 25/0141* (2013.01); *A61M 2025/0166* (2013.01); *A61M 39/10* (2013.01); *A61M 39/1011* (2013.01); *A61M 2039/1022* (2013.01)

(58) Field of Classification Search
CPC .............. A61M 25/0141; A61M 39/10; A61M 39/1011; A61M 2025/0166; A62B 2018/00172; A62B 2018/00178
See application file for complete search history.

(56) References Cited

U.S. PATENT DOCUMENTS

| | | | |
|---|---|---|---|
| 7,878,984 B2* | 2/2011 | Jacobsen | A61M 25/09 600/585 |
| 2002/0103445 A1* | 8/2002 | Rahdert | A61M 25/0045 600/549 |
| 2005/0046186 A1 | 3/2005 | Drescher | |
| 2007/0135810 A1 | 6/2007 | Lee et al. | |
| 2008/0188832 A1* | 8/2008 | Tanioka | A61M 25/0054 604/525 |
| 2010/0063534 A1 | 3/2010 | Kugler et al. | |
| 2010/0206453 A1 | 8/2010 | Leeflang et al. | |
| 2010/0320321 A1 | 12/2010 | Sauermann | |
| 2011/0313417 A1* | 12/2011 | De La Rama | A61B 18/1492 606/41 |
| 2014/0025045 A1 | 1/2014 | Abt et al. | |
| 2018/0093070 A1* | 4/2018 | Cottone | A61M 25/0052 |

FOREIGN PATENT DOCUMENTS

| | | |
|---|---|---|
| EP | 2 351 593 A2 | 8/2011 |
| EP | 2 392 430 A1 | 12/2011 |
| EP | 2 923 723 A1 | 9/2015 |
| JP | S57046872 A | 3/1982 |
| JP | S62147108 A | 7/1987 |
| JP | H2145310 A | 6/1990 |
| JP | 2015526157 A | 9/2005 |
| JP | 2010122991 A | 11/2008 |
| JP | 2017121483 A | 7/2017 |
| JP | WO2018037475 A1 | 9/2018 |
| JP | 2019518306 A | 6/2019 |

OTHER PUBLICATIONS

Written Opinion dated Dec. 9, 2019, International Application No. PCT/IB2019/055360.
International Preliminary Report on Patentability dated Dec. 29, 2020, from corresponding International Application No. PCT/IB2019/055360.
Search Reported dated May 30, 2022, from Corresponding CN Application No. 201980043881.6.
First Office Action Translation dated Jun. 6, 2022, from Corresponding CN Application No. 201980043881.6.
Exam Report dated Feb. 7, 2024, from corresponding European Application No. 19765788.5.
Search Report (English translation) dated Apr. 14, 2023, from corresponding Japanese Application No. 2020-572664.
Notice of Reasons for Refusal (English translation) dated Apr. 18, 2023, from corresponding Japanese Application No. 2020-572664.
Decision to Grant Patent (English translation) dated May 7, 2024, from corresponding Japanese Application No. 2020-572664.

* cited by examiner

CATHETER ELEMENTS FOR BOND-STRENGTH ENHANCEMENT

FIELD OF THE INVENTION

The present invention relates generally to medical probes, and particularly to the design and manufacturing of catheters.

BACKGROUND OF THE INVENTION

Various known structural design elements and processing methods are employed in the design and manufacturing of catheters. U.S. Pat. No. 4,398,910 describes a wound drain catheter comprising a drain portion connected to an outflow tube portion. The drain portion comprises a central core with plural T-shape members projecting therefrom to form plural lumens having respective longitudinal grooves for fluid communication with the wound. The lumens serve as conduits for the fluid, and serve as bending structural members to prevent kinking.

U.S. Patent Application Publication 2007/0135810 describes a catheter for measuring electrical activity and ablating tissue. The catheter comprises an elongated generally-tubular catheter body made of proximal and distal segments of a shaft. A non-retractable electrode assembly is mounted at the distal end of the catheter body. A means for attaching the proximal segment of shaft to the distal segment of shaft is embodied. The proximal end of the distal segment of shaft comprises an outer circumferential notch that receives the inner surface of the outer wall of the proximal the segment of shaft. The distal segment of shaft and proximal segment of shaft are attached by glue or the like. The notches are circumferential, and bonding of segment is thus strong in a particular direction.

U.S. Patent Application Publication 2010/0320321 (brought from avionic industry) describes a method of connecting two fuselage sections arranged with a uniform distribution at a distance from and parallel to one another, with the formation of a transverse joint. In order to be able in particular to join together the fuselage sections so that simple tolerance compensation is made possible in a continuous, industrial production process, the method according to the invention comprises the following steps: aligning a first and a second fuselage section with respect to one another, heating and adapting at least one transverse butt strap, formed by a fiber-reinforced thermoplastic material, in such a way that tolerance compensation between differing cross-sectional geometries of the first and second fuselage sections is made possible, or heating at least one end region of a second fuselage section formed by a fiber-reinforced thermoplastic material, and joining together the two fuselage sections. The result is a single type of joint that can withstand high amounts of force from a single direction.

U.S. Patent Application Publication 2010/0063534 describes devices and methods to visually define a vascular wall boundary, protect a vascular wall boundary from perforation, bypass an occlusion, and/or remove an occlusion. A joint created by overlapping components (e.g. placing the outside diameter of one tubular component circumferentially within the inside diameter of another tubular component) may result in a joint with superior mechanical strength (e.g., the joint may have superior strength to endure the shear force when placed in a bend). Placing tubular components in the described overlapping configuration is commonly referred to as a "lap joint."

SUMMARY OF THE DISCLOSURE

An embodiment of the present invention provides a catheter manufacturing method including the step of providing a hollow cylindrical part of a catheter, having a longitudinal axis, to be bonded to a given part along respective edge surfaces of the hollow cylindrical and the given parts. One or more undercut structures that are disposed circumferentially with respect to the longitudinal axis and also generally parallel to the longitudinal axis, the undercut structures having a radial orientation with respect to the longitudinal axis, are formed at least in the edge surface of the hollow cylindrical part. The hollow cylindrical part and the given part are connected using the undercut structures.

In some embodiments, the step of connecting includes bonding the hollow cylindrical part and the given part with a bonding material that fills the undercut structures. In some embodiments, the step of forming includes forming the undercut structures both in the hollow cylindrical part surface and in the given part surface, wherein the given part is another hollow cylindrical part.

In an embodiment, the hollow cylindrical part and the other hollow cylindrical part are configured to operate as a coupler and as a spring.

In another embodiment, the manufacturing method further includes fitting a flexible circuit between the coupler and the spring, wherein the coupler and the spring are bonded together.

In an embodiment, the step of forming includes forming the undercut structures only in the surface of the hollow cylindrical part and not in the surface of the given part.

In another embodiment, the manufacturing method further includes a step of forming the undercut structures in a same radial setup used for forming one or more additional radial features of the catheter.

In some embodiments, the step of connecting includes interlocking the hollow cylindrical part and the given part.

In some embodiments, the step of forming the one or more undercut structures includes laser cutting at least the edge surface of the hollow cylindrical part to define the undercut structures.

In an embodiment, the step of forming includes machining at least the edge surface of the hollow cylindrical part.

In another embodiment, the step of providing the given part includes providing a plastic component.

In another embodiment, the step of providing includes forming one or more protrusions.

There is additionally provided, in accordance with an embodiment of the present invention, a catheter including a hollow cylindrical part and a given part. The hollow cylindrical part has an edge surface. The given part has an edge surface that faces the edge surface of the hollow cylindrical part, wherein one or more undercut structures, having a radial orientation with respect to the longitudinal axis, are formed at least in the edge surface of the hollow cylindrical part.

The present invention will be more fully understood from the following detailed description of the embodiments thereof, taken together with the drawings in which:

DETAILED DESCRIPTION OF EMBODIMENTS

Overview

Figure 1:
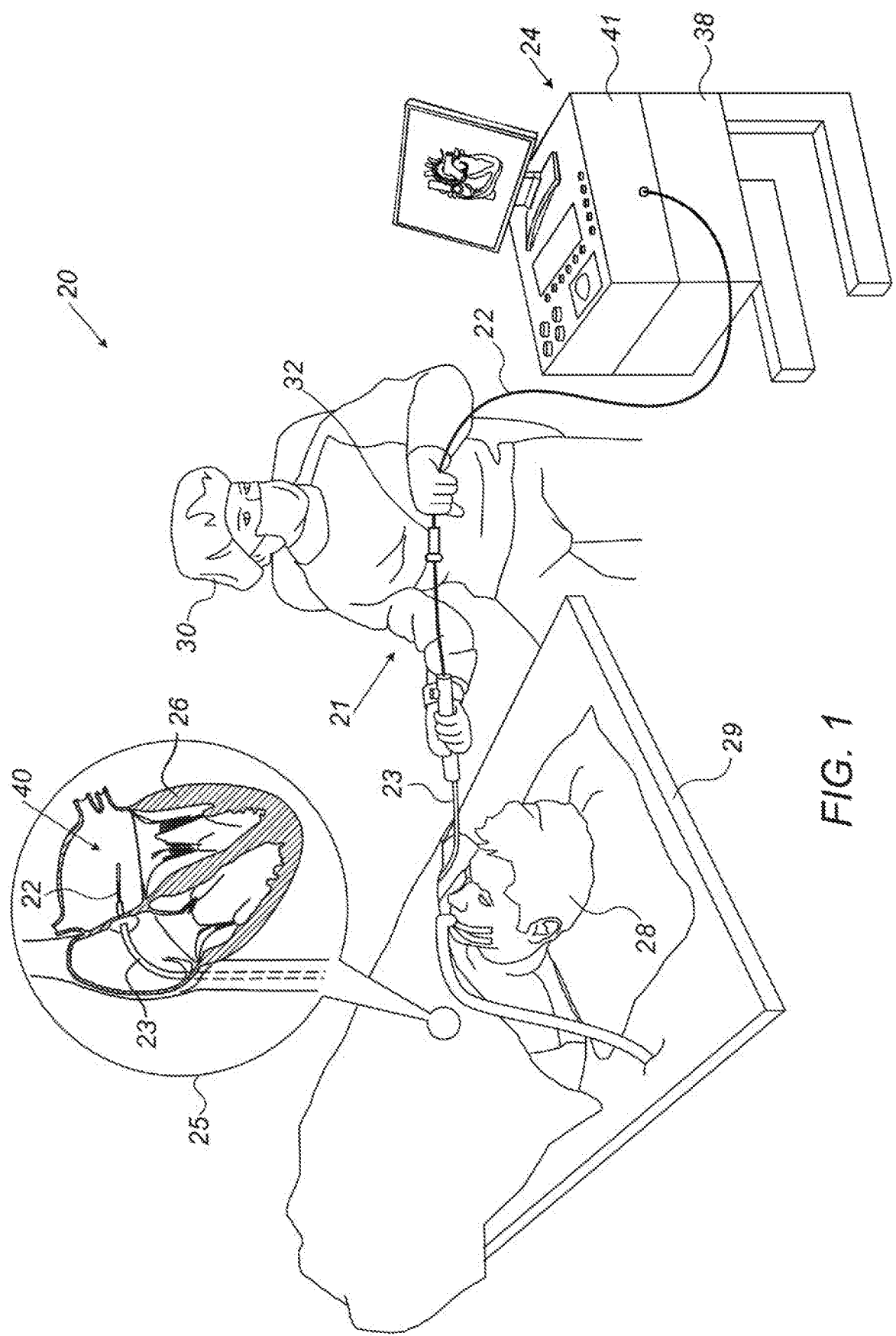
FIG. 1 is a schematic, pictorial illustration of a catherization system, in accordance with an embodiment of the present invention.

Catheter parts that are bonded together, such as parts of a distal end of a catheter, may delaminate due to various forces exerted on the parts. The possibility of delamination is more pronounced for a "butt joint" type bond due to its small surface area relative to the size of the parts it bonds together.

Surface processing, such as bead blasting or chemo-mechanical treatments, can enhance bonding strength by increasing the surface area. Such processing, however, requires additional tooling and fixtures during manufacture, increasing both fabrication time and cost. Furthermore, the resulting treated surfaces still lack consistent mechanical structures, such as overhangs, that can reduce bond delamination.

Embodiments of the present invention that are described hereinafter provide methods for designing and forming undercut structures in edge surfaces of hollow cylindrical catheter parts so as to enhance bond resilience to delaminating forces. Two parts, at least one of which is a hollow cylindrical part that possess such undercut structures, are then connected to one another along their edge surfaces. For example, a bonding material may be applied so as to fill the undercut structures and reinforce the bond.

In the context of the present patent application and in the claims, the term "undercut" is defined as a recess formed in a surface of a mechanical part, wherein (i) the recess has an opening connecting it to the surface and (ii) below the surface, the recess is wider than the opening. Two non-limiting examples of undercuts are T-shape and L-shape recesses.

Typically, a catheter part to be inserted into a blood vessel has a hollow cylindrical shape. In some embodiments, the undercut structures have a radial orientation with respect to longitudinal axis of the catheter parts they are formed in. The radially oriented undercuts assist the bond in withstanding delamination forces from catheter bending and/or twisting in any direction.

In the context of the present patent application and in the claims, the term "radial orientation" means that any point on the edge of the undercut, including the entire wall thickness of the undercut, lies on a radius that is (i) perpendicular to the longitudinal axis of the cylindrical part, and (ii) not obstructed by the wall of the cylindrical part. As such, an undercut having a radial orientation may be formed by a radial machining or laser-cutting setup, possibly the same setup used for machining or laser cutting other radial features of the catheter part.

The undercut structures create interlocking features at the butt joints and therefore prevent delamination by offering compressive reinforcement in addition to the increased tensile strength at the bond interface. For example, a radial patterning of undercuts in the form of T-shapes on a cylinder face of a catheter element provides reinforcement regardless of the bending direction of the butt joint.

In an embodiment, undercuts in a form of T-shape along a circumference offer bond delamination resistance regardless of applied load direction. Undercuts in a form of an L-shape may replace T-shape cuts if bond reinforcement is required in a single direction, i.e., in unidirectional bending. For simplicity and clarity of presentation, the description hereinafter describes particular shapes of undercuts, such as T-shape and/or L-shape. However, there are numerous shapes possible, all of which are incorporated in this application and are within the meaning intended by applicant of the term "undercut" or "undercut structure" (and all its variations) as used herein.

The radially-oriented undercut structures can be formed as part of a manufacturing process used for processing of other radial features of a catheter part. For example, bond enhancing undercut structures can be formed into the material of a catheter part in a same radial setup. Such setup may use machining or laser-cutting for processing both the undercut structures and the additional radial features.

In a typical manufacturing process, the bonding material comprises a cement, which is applied to the edge surfaces of the parts, so as to fill the undercuts. The two parts may then be held pressed one against the other and any excess cement removed. The applied cement may then undergo a process of drying and/or curing. Cements suitable for filling the undercuts may be of polyurethane adhesive, epoxy type, rubber cements, UV-curing cements and the like which has the ability to form a bond to connect two discrete parts.

In some embodiments, bond-strength enhancing structures, such as T-shape and/or L-shape undercuts, can be laser cut, drilled, or etched, among other manufacturing methods. Cutting bond-strength enhancing structures in various forms in the same setup as other radial features eliminates the need for creating secondary setups that use an abrasive tool or chemical etching to increase surface area in butt joints.

The disclosed technique for achieving bonds between catheter parts, in which the bonds are designed to be highly resilient to delaminating stresses (i.e., forces), may increase the design options of catheter designers, so as to yield better and safer catheter distal ends.

System Description

FIG. 1 is a schematic, pictorial illustration of a catherization system 20, in accordance with an embodiment of the present invention. System 20 comprises a catheter 21, wherein, as inset 25 shows, a distal end of a shaft 22 of the catheter is inserted through a sheath 23 into a heart 26 of a patient 28 lying on a table 29. The proximal end of catheter 21 is connected to a control console 24. In the embodiment described herein, catheter 21 may be used for any suitable therapeutic and/or diagnostic purpose, such as electrical sensing, balloon angioplasty, and ablation of tissue in heart 26, among other possible medical usages of a cardiac catheter. As exemplified in FIG. 1, the distal end of shaft 22 comprises a distal tip 40 comprising electrodes for electrophysiological sensing and/or for radiofrequency ablation. As used herein, the term "proximal" indicates a location closer to the operator whereas "distal" indicates a location further away to the operator or physician 30.

Physician 30 navigates the distal end of shaft 22 to a target location in heart 26 by manipulating shaft 22 using a manipulator 32 near the proximal end of the catheter and/or deflection from sheath 23.

Control console 24 comprises a processor 41, typically a general-purpose computer with a suitable front end and interface circuits 38 for receiving signals from catheter 21, as well as for applying treatment via catheter 21 in heart 26 and for controlling the other components of system 20. Processor 41 typically comprises a general-purpose computer with software programmed to carry out the functions described herein. The software may be downloaded to the computer in electronic form, over a network, or it may, alternatively or additionally, be provided and/or stored on non-transitory tangible media, such as magnetic, optical, or electronic memory.

The example configuration shown in FIG. 1 is chosen purely for the sake of conceptual clarity. The disclosed techniques may similarly be applied using other system components and settings. For example, system 20 may comprise other components and perform non-cardiac treatments.

Catheter Elements for Bond-Strength Enhancement

Figure 2A:
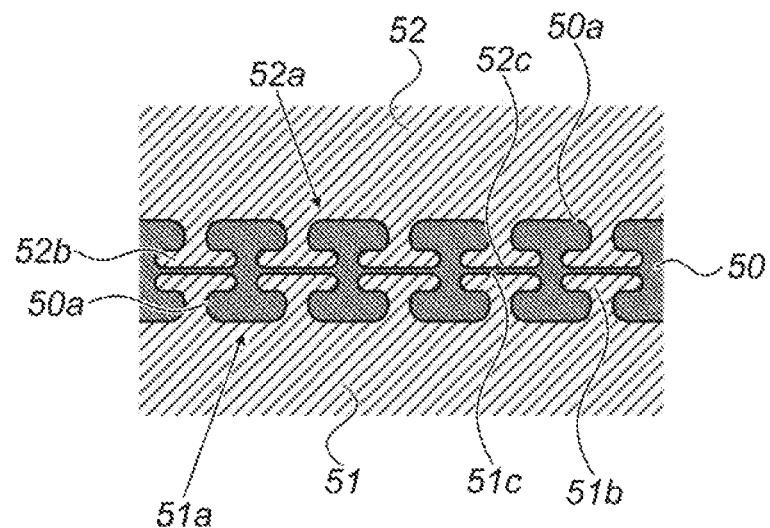
FIGS. 2A and 2B are cross-sectional illustrative views of interfaces between bonded catheter parts that comprise undercut structures, in accordance with embodiments of the present invention.
Figure 2B:
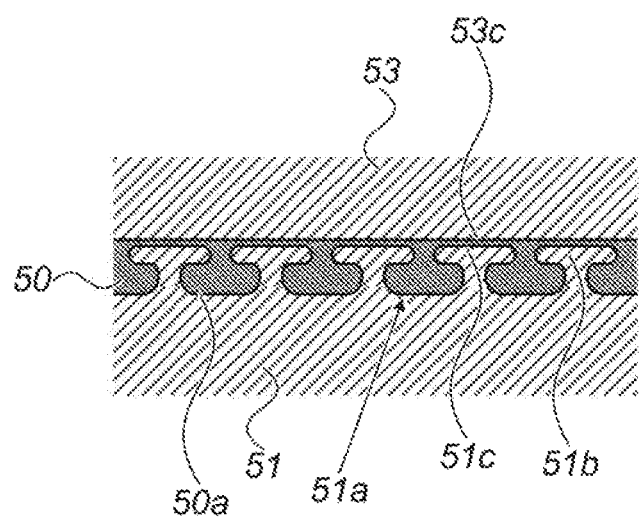

FIGS. 2A and 2B are cross-sectional illustrative views of interfaces between bonded catheter parts that comprise undercut structures, in accordance with embodiments of the present invention. FIG. 2A shows a part 51 and a part 52 bonded together with, for example, an epoxy cement 50. Part 51 and part 52 are cemented together along an interface defined by edge surface 51c of part 51 and edge surface 52c of part 52. In order to mitigate the risk of delamination of the epoxy layer, parts 51 and 52 are both patterned with T-shape undercut structures 51a and 52a (having overhangs 51b and 52b, respectively), done, for example, during the machining of parts 51 and 52. As seen, this creates recess volumes 50a for the epoxy 50 to fill, so that epoxy 50 may provide enhanced tensile strength at the bonded interfaces. Furthermore, epoxy 50 creates interlocking features at the butt joints of parts 51 and 52, preventing bond delamination by offering compressive reinforcement, in addition to the increased tensile strength at the bonded interfaces 51c and 52c.

FIG. 2B exemplifies part 51 and a part 53 cemented together by epoxy 50 along an interface defined by edge surface 51c of part 51 and edge surface 53c of part 53. Part 53 has sufficient affinity to epoxy 50 so that epoxy 50 bond to part 53 poses no risk of delamination. Therefore, as compared to part 51 (in which similarly referenced part numbers have the same meaning as part 51 in FIG. 2A), part 53 does not require any bond-strength enhancing structures, such as bonding material filled undercuts. That is, the undercut structures 51a are formed only in the first surface (of part 51) and not in the second surface (of part 53).

The illustrations shown in FIGS. 2A and 2B are chosen purely for the sake of conceptual clarity. For example, if the tendency to delaminate has a similar effect over multiple directions, a mushroom-shape undercut, with a T-shape cross section in each direction, may be used. Where the risk of delamination is enhanced by multiple distinct directions, various polygon shapes may be used in forming undercuts. Where the strain is unidirectional, an L-shape undercut may be found optimal.

Alternating shapes, such as adjacent T-shape undercuts alternately rotated by a right angle with respect to each other, may be used such that each pair of T-shape structures provides resistance to delamination along two perpendicular axes. Similarly, more than two shapes may be interleaved, e.g., a triplet of shapes that mitigates bond delamination risk along three directions.

Figure 3:
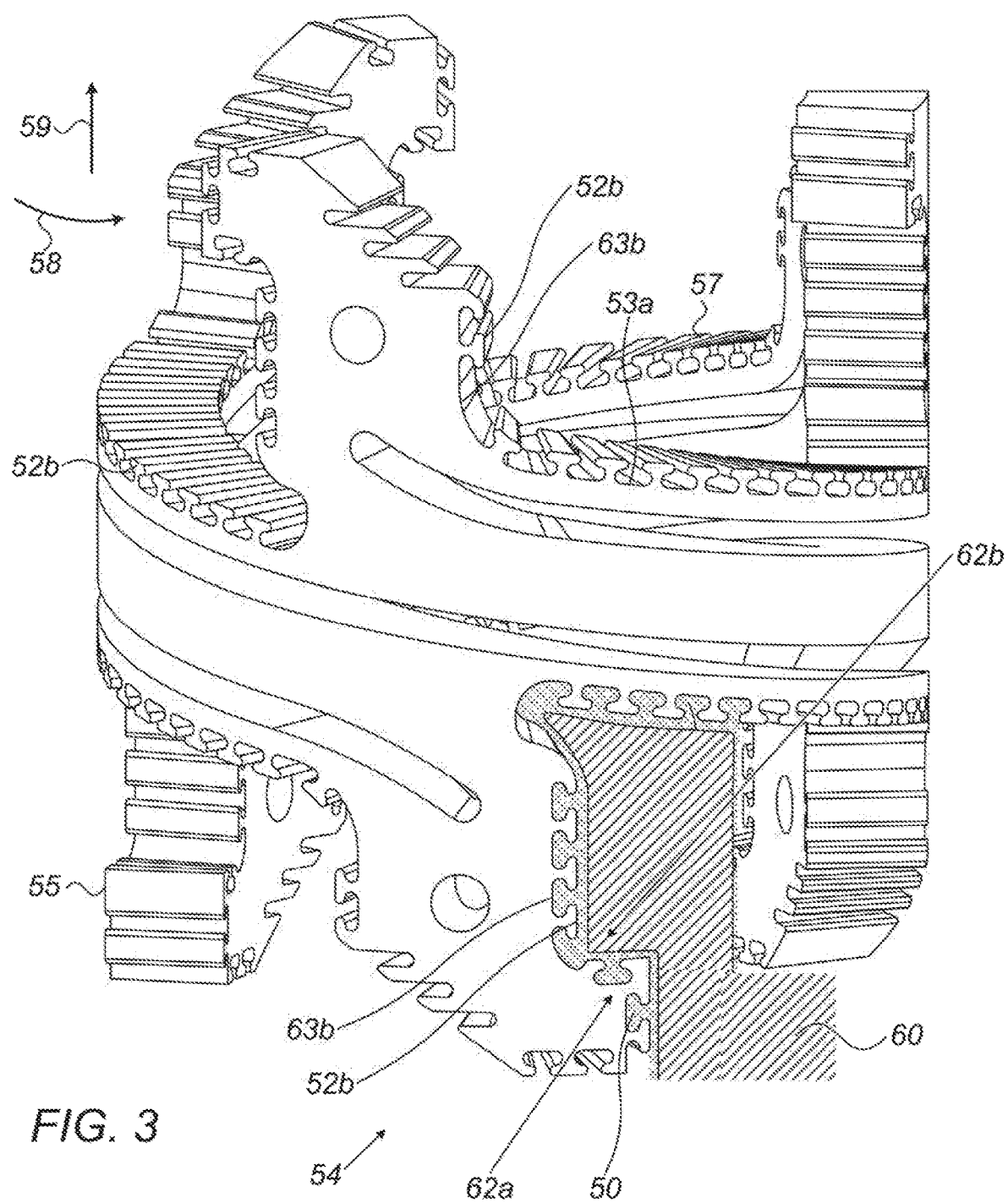
FIG. 3 is a volume rendering of a hollow catheter part comprising bond-strength enhancing undercut structures, in accordance with an embodiment of the present invention.

FIG. 3 is a volume rendering of a hollow catheter part 54 comprising bond-strength enhancing undercut structures, in accordance with an embodiment of the present invention. As seen, T-shape bond-strength enhancing undercut structures 55 are designed to assist bonds applied to the part to withstand delamination due to axial forces (such as shaft 22 bending relative to a longitudinal axis 59).

The patterning of the T-shape undercuts on edge surfaces of the largely cylindrically-shape part 54, while keeping a radial orientation, as defined above, of the undercut structures over the circumferences, offers reinforcement regardless of the bending direction of its butt joints. T-shape undercut structures 57 are designed to assist withstanding delaminating forces from shaft 22 bending and/or twisting, that the bonds may experience (e.g., due to delamination forces along an azimuthal axis 58).

A seen in FIG. 3, a given part 60, for example, a plastic molded part, is bonded with epoxy 50 to part 54. Plastic molded part 60 is shaped to have a radial orientation with respect to longitudinal axis 59, and has an edge surface that faces the edge surface of hollow cylindrical part 54, where the edge of part 54 comprises undercut structures. Epoxy 50 fills undercut structures of part 54, so as to reinforce the bond as described above.

In some embodiments, part 54 includes "bayonet mount" features 62a (e.g., protrusions), to provide mechanical strength enhancement when mated to plastic components, such as given part 60, which have mating "bayonet mount" features 62b on them. It is noted that the edge surface 63a of hollow cylindrical member 54 is provided generally proximal to the circumference (with respect to longitudinal axis 59) of member 54. As well, edge surface 63b is also provided for member 54 such that edge surface 63b are proximate to the circumference of member 54 and also aligned generally parallel to the longitudinal axis. Both edge surfaces 63a and 63b may be formed so that these edge surfaces may be viewed as one continuous edge surface. The arrangement of edge surfaces 63a and 63b with undercut structures 52b allows for a very strong bond with another cylindrical part that would resist delamination or separation of the bonded parts for all six degrees-of-freedom (i.e., all directions), which is believed to be heretofore not known in the field. Alternatively or additionally to filling the undercuts, epoxy 50 affixes plastic components mated with the strength enhancement "bayonet mount" features. As seen, protrusions 62a and 62b provides longitudinal interlocking of bonded parts 54 and 60.

The example shown in FIG. 3 is chosen purely for the sake of conceptual clarity. In alternative embodiments various distal parts of a catheter may include variously shaped structures requiring undercut bonds to withstand delamination from multiple directions and/or from continuous directions, such as over an entire circumference, as elaborated above.

Figure 4:
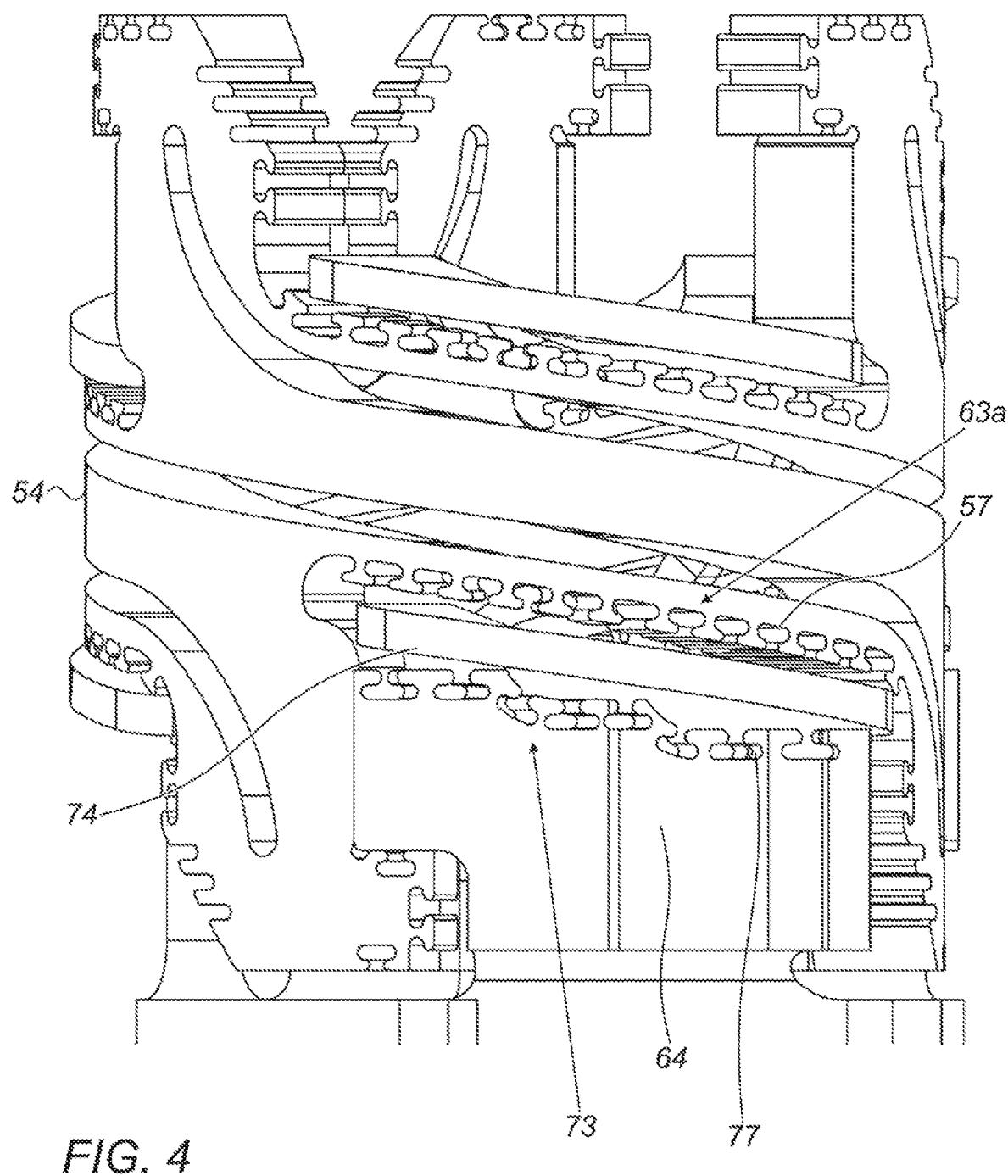
FIG. 4 is a volume rendering of two hollow catheter parts which are configured to be bonded together with an intermediate flexible circuit, in accordance with an embodiment of the present invention.

FIG. 4 is a volume rendering of two hollow catheter parts 54 and 64, which are configured to be bonded together with an intermediate flexible circuit 74, in accordance with an embodiment of the present invention. As seen, hollow catheter part 54 has T-shape undercut structures 57 at its edge surface 63a, while hollow catheter part 64 has T-shape undercut structures 77 at its edge surface 73. In an embodiment, hollow catheter part 54 is a coupler, and hollow catheter part 64 is a spring. As seen in FIG. 4, coupler 54, spring 64, and flexible circuit 74 fitted in between, are assembled together. When bonded together with, for example, epoxy 50, parts 54, 64 and 74 create a strong and flexible member of a catheter. The structural reinforcement is provided, among other means, by undercuts 57 and 77. In an embodiment, flexible circuit 74 is bonded as described above, so as to provide electronic circuitry and wiring to devices fitted at a tip of the catheter. In an embodiment, flexible circuit 74 comprises electronic devices, such as preamplifiers, so as to amplify sensed electrophysiological signals, sensed temperature signals, and comprises interconnects for applying radiofrequency ablation energy.

Figure 5:
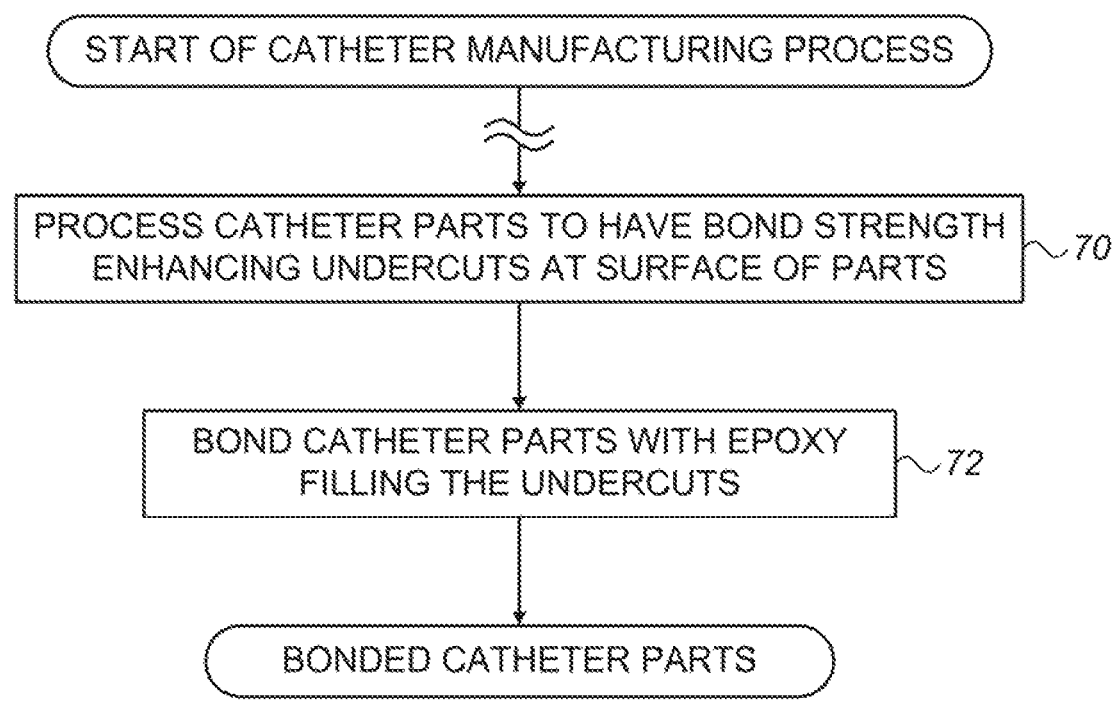
FIG. 5 is a flow chart of a catheter manufacturing method comprising bonding of hollow catheter parts using undercut structures, in accordance with an embodiment of the present invention.

FIG. 5 is a flow chart of a catheter manufacturing method comprising bonding of hollow catheter parts using undercut structures, in accordance with an embodiment of the present invention. In general, there are manufacturing step which precede the disclosed manufacturing steps, and which are not shown for simplicity of presentation.

At a mechanical processing step 70, hollow catheter parts are processed (e.g., machined and/or laser-cut) to have bond strength enhancing undercut structures at their edge surfaces. The undercut structures may be formed with a radial orientation, as defined above. Next, at a bonding step 72, the hollow catheter parts are bonded together with epoxy, wherein the epoxy fills the undercuts, in way similar to that shown with epoxy 50 filling undercuts 51a and 51b of bonded parts 51 and 52. The resulting bonded catheter part are then available for further manufacturing steps, such as an assembly, which are also not shown.

The example flow chart shown in FIG. 5 is chosen purely for the sake of conceptual clarity. In practice, manufacturing stages and manufacturing methods may substantially differ from that presented in this highly simplified flow chart, for instance the bond strength enhancing undercuts may be created at the time of manufacturing the hollow cylindrical part, and be present on the hollow cylindrical part at the beginning of the catheter assembly process.

Although the embodiments described herein mainly address design and manufacturing of cardiac catheters, the methods and systems described herein can also be used in other applications, such as in otolaryngology or neurology procedures.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A catheter, comprising:
   a hollow cylindrical coupler comprising:
      a wall extending along a longitudinal axis, the wall comprising an edge surface;
      a plurality of undercut structures formed in the edge surface and disposed circumferentially about the longitudinal axis; and
      a lumen extending therethrough;
   a spring; and
   a flexible circuit fitted between the coupler and the spring, wherein the coupler, flexible circuit and the spring are bonded together with bonding material, which is applied along the edge surface and the spring and fills each undercut structure of the plurality of undercut structures.

2. The catheter according to claim 1, further comprising another plurality of undercut structures formed in an edge surface of the spring.

3. The catheter according to claim 1, wherein the undercut structures are formed only in the edge surface of the hollow cylindrical coupler and not in an edge surface of the spring.

4. The catheter according to claim 1, wherein the coupler is configured to withstand delamination forces from catheter bending or twisting.

5. The catheter according to claim 1, wherein the flexible circuit is configured to provide electronic circuitry and wiring to a device fitted at a tip of the catheter.

6. The catheter according to claim 1, wherein the bonding material is epoxy.

7. The catheter according to claim 1, wherein each undercut structure of the plurality of undercut structures comprises a T-shape.

8. The catheter according to claim 7, wherein each undercut structure comprises a recess volume within which the bonding material fills.

9. The catheter according to claim 8, further comprising a plurality of overhangs, wherein adjacent overhangs of the plurality of overhangs at least partially define the T-shape of each respective undercut structure.

10. The catheter according to claim 1, the coupler comprising one or more protrusions, the edge surface running along the one or more protrusions.

11. The catheter according to claim 10, wherein one or more undercut structures of the plurality of undercut structures are formed in the one or more protrusions.

12. The catheter according to claim 1, the spring comprising an edge surface, the edge surface of the spring facing the edge surface of the coupler.

13. The catheter according to claim 12, the bonding material being applied along an interface defined by the edge surface of the spring and the edge surface of the coupler.

14. The catheter according to claim 13, a butt joint between the coupler and the spring being defined at the interface of the edge surface of the spring and the edge surface of the coupler.

* * * * *